United States Patent
Luciano, Jr.

(10) Patent No.: US 9,015,058 B2
(45) Date of Patent: *Apr. 21, 2015

(54) MATRIX BASED DOSAGE SCHEDULING

(75) Inventor: Robert Luciano, Jr., Reno, NV (US)

(73) Assignee: Edge Medical Properties, LLC, Reno, NV (US)

( * ) Notice: Subject to any disclaimer, the term of this patent is extended or adjusted under 35 U.S.C. 154(b) by 316 days.

This patent is subject to a terminal disclaimer.

(21) Appl. No.: 13/312,907

(22) Filed: Dec. 6, 2011

(65) Prior Publication Data

US 2012/0089416 A1    Apr. 12, 2012

Related U.S. Application Data

(63) Continuation-in-part of application No. 12/945,709, filed on Nov. 12, 2010, which is a continuation-in-part of application No. 12/896,284, filed on Oct. 1, 2010, application No. 13/312,907, which is a (Continued)

(51) Int. Cl.
*G06Q 30/00*   (2012.01)
*G06F 19/00*   (2011.01)
*G06Q 30/06*   (2012.01)
*G06Q 50/22*   (2012.01)

(52) U.S. Cl.
CPC ........ *G06F 19/3456* (2013.01); *G06F 19/3462* (2013.01); *G06F 19/3481* (2013.01); *G06Q 30/0633* (2013.01); *G06Q 30/0643* (2013.01); *G06Q 30/0635* (2013.01); *G06Q 30/0641* (2013.01); *G06Q 50/22* (2013.01)

(58) Field of Classification Search
CPC .......... G06Q 30/0633; G06Q 30/0635; G06Q 30/0641; G06Q 30/0643; G06F 19/3456; G06F 19/3462; G06F 19/3481
USPC ................. 705/26.1, 2, 3, 27.1, 26.8, 51, 500
See application file for complete search history.

(56) References Cited

U.S. PATENT DOCUMENTS

| | | | |
|---|---|---|---|
| 2,294,220 | A | 8/1942 | Albertson |
| 3,254,828 | A | 6/1966 | Lerner |
| 3,432,951 | A | 3/1969 | Cherrin |
| 3,497,982 | A | 3/1970 | Schultz |
| 3,503,493 | A | 3/1970 | Nagy |
| 3,703,955 | A | 11/1972 | Inacker |

(Continued)

FOREIGN PATENT DOCUMENTS

| | | |
|---|---|---|
| DE | 3502647 A1 | 7/1986 |
| WO | WO 96/13790 A1 | 5/1996 |

(Continued)

*Primary Examiner* — Yogesh C Garg

(74) *Attorney, Agent, or Firm* — Michael A. Kerr; Kerr IP Group, LLC

(57) ABSTRACT

A system and method for scheduling tablet dosage is described. The system includes a computing device, a filling system, and a plurality of containers. The computing device hosts an application that includes a user interface receiving a prescription order including a designation for each tablet to be ordered. In one embodiment, the system and method also includes an automated inspection module that performs an inspection of each container to identify a first tablet and a second tablet within each container. In another illustrative embodiment, each container includes a pouch with a plurality of different tablets. Additionally, the plurality of pouches may be received by a box.

25 Claims, 10 Drawing Sheets

Related U.S. Application Data continuation-in-part of application No. 12/896,275, filed on Oct. 1, 2010, now Pat. No. 8,914,298, and a continuation-in-part of application No. 12/896,134, filed on Oct. 1, 2010, now Pat. No. 8,712,582, and a continuation-in-part of application No. 12/891,042, filed on Sep. 27, 2010, and a continuation-in-part of application No. 12/891,029, filed on Sep. 27, 2010, which is a continuation-in-part of application No. 12/696,884, filed on Jan. 29, 2010, now Pat. No. 8,931,241, application No. 13/312,907, which is a continuation-in-part of application No. 12/684,640, filed on Jan. 8, 2010, and a continuation-in-part of application No. 12/684,664, filed on Jan. 8, 2010, and a continuation-in-part of application No. 12/684,060, filed on Jan. 7, 2010, now Pat. No. 8,789,700, which is a continuation-in-part of application No. 11/796,123, filed on Apr. 25, 2007, now Pat. No. 7,690,173, application No. 13/312,907, which is a continuation-in-part of application No. 12/631,586, filed on Dec. 4, 2009, now Pat. No. 8,777,012, and a continuation-in-part of application No. 12/424,483, filed on Apr. 15, 2009, which is a continuation-in-part of application No. 11/923,321, filed on Oct. 24, 2007, now Pat. No. 8,266,878, which is a continuation-in-part of application No. 11/796,123, and a continuation-in-part of application No. 11/796,124, filed on Apr. 25, 2007, now Pat. No. 8,074,426, and a continuation-in-part of application No. 11/796,125, filed on Apr. 25, 2007, said application No. 12/424,483 is a continuation-in-part of application No. 11/241,783, filed on Sep. 30, 2005, now Pat. No. 8,123,036, application No. 13/312,907, which is a continuation-in-part of application No. 12/424,475, filed on Apr. 15, 2009, now Pat. No. 8,146,747, and a continuation-in-part of application No. 12/418,436, filed on Apr. 3, 2009, now abandoned, and a continuation-in-part of application No. 12/418,418, filed on Apr. 3, 2009, now abandoned, said application No. 11/796,124 is a continuation-in-part of application No. 11/796,125, application No. 13/312,907, which is a continuation-in-part of application No. 12/418,422, filed on Apr. 3, 2009, now abandoned, and a continuation-in-part of application No. 11/923,321, filed on Oct. 24, 2007, now Pat. No. 8,266,878, and a continuation-in-part of application No. 11/796,124, filed on Apr. 25, 2007, now Pat. No. 8,074,426, which is a continuation-in-part of application No. 11/241,783, filed on Sep. 30, 2005, now Pat. No. 8,123,036.

(60) Provisional application No. 61/420,140, filed on Dec. 6, 2010, provisional application No. 61/420,151, filed on Dec. 6, 2010, provisional application No. 61/486,427, filed on May 16, 2011, provisional application No. 61/486,436, filed on May 16, 2011, provisional application No. 61/498,489, filed on Jun. 17, 2011, provisional application No. 61/248,471, filed on Oct. 4, 2009, provisional application No. 61/245,912, filed on Sep. 25, 2009, provisional application No. 61/245,899, filed on Sep. 25, 2009, provisional application No. 61/045,160, filed on Apr. 15, 2008, provisional application No. 61/045,166, filed on Apr. 15, 2008, provisional application No. 61/045,171, filed on Apr. 15, 2008, provisional application No. 60/795,370, filed on Apr. 26, 2006, provisional application No. 60/795,446, filed on Apr. 26, 2006, provisional application No. 60/795,413, filed on Apr. 26, 2006, provisional application No. 60/854,341, filed on Oct. 24, 2006, provisional application No. 61/042,262, filed on Apr. 3, 2008, provisional application No. 61/042,263, filed on Apr. 3, 2008, provisional application No. 60/615,267, filed on Oct. 1, 2004.

(56) References Cited

U.S. PATENT DOCUMENTS

| | | |
|---|---|---|
| 3,780,856 A | 12/1973 | Braverman |
| 3,921,804 A | 11/1975 | Tester |
| 3,933,245 A | 1/1976 | Mullen |
| 4,039,080 A | 8/1977 | Cappuccilli |
| 4,062,445 A | 12/1977 | Moe |
| 4,318,477 A | 3/1982 | Kerpe |
| 4,416,375 A | 11/1983 | Braverman et al. |
| 4,512,476 A | 4/1985 | Herrington, Jr. |
| 4,535,890 A | 8/1985 | Artusi |
| 4,546,901 A | 10/1985 | Buttarazzi |
| 4,655,026 A | 4/1987 | Wigoda |
| 4,693,371 A | 9/1987 | Malpass |
| 4,749,085 A | 6/1988 | Denney |
| 4,799,590 A | 1/1989 | Furman |
| 4,805,800 A | 2/1989 | Nocek et al. |
| 4,850,489 A | 7/1989 | Weithmann et al. |
| 4,867,315 A | 9/1989 | Baldwin |
| 4,872,559 A | 10/1989 | Schoon |
| 4,887,790 A | 12/1989 | Wilkinson et al. |
| 4,918,604 A | 4/1990 | Baum |
| 4,953,745 A | 9/1990 | Rowlett, Jr. |
| 4,972,657 A | 11/1990 | McKee |
| 5,014,851 A | 5/1991 | Wick |
| 5,186,345 A | 2/1993 | Ching An |
| 5,195,123 A | 3/1993 | Clement |
| 5,199,636 A | 4/1993 | Young |
| 5,310,057 A | 5/1994 | Caldwell et al. |
| 5,366,087 A | 11/1994 | Bane |
| 5,390,796 A | 2/1995 | Kerfoot, Jr. |
| 5,457,895 A | 10/1995 | Thompson et al. |
| 5,558,229 A | 9/1996 | Halbich |
| 5,577,612 A | 11/1996 | Chesson et al. |
| 5,597,995 A | 1/1997 | Williams et al. |
| 5,642,906 A | 7/1997 | Foote et al. |
| 5,671,592 A | 9/1997 | Yuyama et al. |
| 5,737,539 A | 4/1998 | Edelson et al. |
| 5,788,079 A | 8/1998 | Bouthiette |
| D400,412 S | 11/1998 | Gold |
| 5,878,887 A | 3/1999 | Parker et al. |
| 5,883,370 A | 3/1999 | Walker et al. |
| 5,899,333 A | 5/1999 | Williams et al. |
| 5,963,453 A | 10/1999 | East |
| 5,995,938 A | 11/1999 | Whaley |
| 6,012,582 A | 1/2000 | Haygeman et al. |
| 6,115,996 A | 9/2000 | Yuyama et al. |
| 6,155,423 A | 12/2000 | Katzner et al. |
| 6,155,485 A | 12/2000 | Coughlin et al. |
| 6,202,923 B1 | 3/2001 | Boyer et al. |
| 6,273,260 B1 | 8/2001 | ColDepietro et al. |
| 6,293,403 B1 | 9/2001 | Holmberg |
| 6,308,494 B1 | 10/2001 | Yuyama et al. |
| 6,318,630 B1 | 11/2001 | Coughlin et al. |
| 6,324,253 B1 | 11/2001 | Yuyama et al. |
| 6,343,695 B1 | 2/2002 | Petrick et al. |
| D455,057 S | 4/2002 | Medhurst |
| 6,371,297 B1 | 4/2002 | Cha |
| 6,401,919 B1 | 6/2002 | Griffis et al. |
| 6,449,927 B2 | 9/2002 | Hebron et al. |
| 6,460,693 B1 | 10/2002 | Harrold |
| 6,505,461 B1 | 1/2003 | Yasunaga |
| 6,523,694 B2 | 2/2003 | Lux, Jr. et al. |
| 6,535,637 B1 | 3/2003 | Wootton et al. |
| 6,581,798 B2 | 6/2003 | Liff et al. |
| 6,662,081 B1 | 12/2003 | Jacober et al. |
| 6,681,935 B1 | 1/2004 | Lewis |
| 6,711,460 B1 | 3/2004 | Reese |
| 6,735,497 B2 | 5/2004 | Wallace et al. |

(56) References Cited

U.S. PATENT DOCUMENTS

| | | |
|---|---|---|
| 6,738,723 B2 | 5/2004 | Hamilton |
| 6,757,898 B1 | 6/2004 | Ilsen et al. |
| 6,771,369 B2 | 8/2004 | Rzasa et al. |
| 6,892,512 B2 | 5/2005 | Rice et al. |
| 6,925,774 B2 | 8/2005 | Peterson |
| 6,981,592 B2 | 1/2006 | Siegel |
| 7,006,893 B2 | 2/2006 | Hart et al. |
| 7,010,899 B2 | 3/2006 | McErlean et al. |
| 7,028,723 B1 | 4/2006 | Alouani et al. |
| 7,055,294 B1 | 6/2006 | Lewis |
| 7,111,780 B2 | 9/2006 | Broussard et al. |
| 7,185,476 B1 | 3/2007 | Siegel et al. |
| 7,225,597 B1 | 6/2007 | Knoth |
| 7,398,279 B2 | 7/2008 | Muno et al. |
| 7,426,814 B2 | 9/2008 | Knoth |
| 7,509,787 B2 | 3/2009 | Ballestrazzi et al. |
| 7,668,730 B2 | 2/2010 | Reardan et al. |
| 2002/0029223 A1 | 3/2002 | Rice et al. |
| 2002/0042725 A1 | 4/2002 | Mayaud |
| 2002/0066691 A1 | 6/2002 | Varon |
| 2002/0117405 A1 | 8/2002 | Wang et al. |
| 2003/0018495 A1 | 1/2003 | Sussman |
| 2003/0136698 A1 | 7/2003 | Klatt |
| 2003/0193185 A1 | 10/2003 | Valley et al. |
| 2003/0200726 A1 | 10/2003 | Rast |
| 2004/0011961 A1 | 1/2004 | Platt et al. |
| 2004/0069675 A1 | 4/2004 | Stevens |
| 2004/0088187 A1 | 5/2004 | Chudy et al. |
| 2004/0122713 A1 | 6/2004 | Hill, Sr. et al. |
| 2004/0158507 A1 | 8/2004 | Meek et al. |
| 2004/0162634 A1 | 8/2004 | Rice et al. |
| 2004/0172295 A1 | 9/2004 | Dahlin et al. |
| 2004/0188998 A1 | 9/2004 | Henthorn |
| 2004/0217038 A1 | 11/2004 | Gibson |
| 2004/0225528 A1 | 11/2004 | Brock |
| 2004/0243445 A1 * | 12/2004 | Keene ................................ 705/2 |
| 2004/0256277 A1 | 12/2004 | Gedanke |
| 2005/0021367 A1 | 1/2005 | Saeger et al. |
| 2005/0049746 A1 | 3/2005 | Rosenblum |
| 2005/0049747 A1 | 3/2005 | Willoughby et al. |
| 2005/0060197 A1 | 3/2005 | Mayaud |
| 2005/0061825 A1 | 3/2005 | Willoughby et al. |
| 2005/0144038 A1 | 6/2005 | Tamblyn et al. |
| 2005/0171813 A1 | 8/2005 | Jordan |
| 2005/0209879 A1 | 9/2005 | Chalmers |
| 2005/0218152 A1 | 10/2005 | Simon |
| 2006/0122729 A1 | 6/2006 | Murphy et al. |
| 2007/0173971 A1 | 7/2007 | Richardson et al. |
| 2008/0059228 A1 * | 3/2008 | Bossi et al. ........................ 705/2 |
| 2008/0190076 A1 | 8/2008 | Klingel et al. |
| 2011/0161097 A1 * | 6/2011 | Fox et al. ........................... 705/2 |
| 2011/0264465 A1 * | 10/2011 | Lindsay ............................. 705/3 |
| 2012/0022893 A1 * | 1/2012 | Findlay et al. .................... 705/3 |
| 2012/0116579 A1 * | 5/2012 | Shows et al. ................. 700/236 |
| 2012/0158430 A1 * | 6/2012 | MacDonald ....................... 705/3 |

FOREIGN PATENT DOCUMENTS

| | | |
|---|---|---|
| WO | WO 2004/082561 A1 | 9/2004 |
| WO | WO 2005/102841 | 11/2005 |

* cited by examiner

| | Wednesday | Thursday | Friday | Saturday | Sunday | Monday | Tuesday |
|---|---|---|---|---|---|---|---|
| | | | 04.00 | | | 04.00 | |
| | | 04.00 | | | 04.00 | | |
| | 04.00 | | | | | | |
| | | | | | | | |
| | | | | | | | |

Period Code: CA
Period Name: Morning
Time of Day: 8:00
☐ Custom Days    Color
☑ Days of Week    Wednesday Offset: 2
Quantity: 4
Interval: 3
Repetitions: 5

Additive    Overwrite

Save    20.0    Cancel

Figure 2

| Period Code | CA ▼ | | Offset | 0 | ⎯128 |
| Period Name | Morning ▼ | | Quantity | 1 | ⎯130 |
| Time of Day | 8:00 | | Interval | 1 | ⎯132 |
| ☑ Custom Days | Color | | Repetitions | 7 | ⎯134 |
| ☐ Days of Week | ▼ | | Additive | Overwrite | ⎯136 |

126 ⎯

| 01.00 | 01.00 | 01.00 | 01.00 | 01.00 | 01.00 | 01.00 |
|---|---|---|---|---|---|---|
|  |  |  |  |  |  |  |
|  |  |  |  |  |  |  |
|  |  |  |  |  |  |  |
|  |  |  |  |  |  |  |

| Save | 7.0 | Cancel |

Figure 3A

| Period Code | CA ▼ | | Offset | 7 | |
| --- | --- | --- | --- | --- | --- |
| Period Name | Morning ▼ | | Quantity | 2 | |
| Time of Day | 8:00 | | Interval | 1 | |
| ☑ Custom Days | Color | | Repetitions | 14 | |
| ☐ Days of Week | ▼ | | Additive | Overwrite | |

| 01.00 | 01.00 | 01.00 | 01.00 | 01.00 | 01.00 | 01.00 |
| --- | --- | --- | --- | --- | --- | --- |
| 02.00 | 02.00 | 02.00 | 02.00 | 02.00 | 02.00 | 02.00 |
| 02.00 | 02.00 | 02.00 | 02.00 | 02.00 | 02.00 | 02.00 |
|  |  |  |  |  |  |  |
|  |  |  |  |  |  |  |

Save   21.0   Cancel

410
408
406
Wednesday ▼    Matrix

| | |
|---|---|
| RX #: 1764 | ☐ |
| Smith, Jane (1/1/1970) | ☐ |
| 1000 Patient Way | ☐ |
| Reno, NV 89503 | ☐ |
| DOB: 12/10/25 | ☐ |
| Written: 10/10/10 | ☐ |
| Filled: 10/11/10 | ☐ |
| Expires: 4/1/10 | ☐ |
| Written for: Depakote 500 MG TAB | ☐ |
| Dispensed for: Depakote 500 MG TAB | ☐ |
| NDC: XXXXXXXXXXX | ☐ |
| Qty: 60 | ☐ |
| Refills: 0 | ☐ |
| DAW Code:00 | ☐ |
| Pharmacist: KJONES | ☐ |
| DOE, JOHN | ☐ |
| DEA #: XXXXXXXXXX | ☐ |
| (775) 444-4321 | ☐ |
| HOA: BID | ☐ |
| TAKE 1 TABLET AT BEDTIME FOR 1 WEEK, . . . | ☐ |

404

402

Dr. John Doe
100 Innovation Blvd.
Incline Village, NV 89851
Telephone: (775) 555-4321

DEA #: XXXXXXXXXX

Date: 10/10/2010

Patient Name: Jane Smith
DOB: 1/1/1970
Address: 1000 Patient Way
         Reno, NV 89503

Rx: Depakote, ER 500mg
    1 tablet q HS x 1wk,
    2 tablets q HS
              disp # 60

Refill  0  Times

Signature: John Doe MD

Approve — 412

Figure 4

| Wednesday | Thursday | Friday | Saturday | Sunday | Monday | Tuesday |
|---|---|---|---|---|---|---|
|  |  | 04.00 |  |  | 04.00 |  |
|  | 04.00 |  |  | 04.00 |  |  |
|  |  |  |  |  |  |  |
|  |  |  |  |  |  |  |
|  |  |  |  |  |  |  |

| Save | | 16.0 | | | Cancel | |

Figure 5

MATRIX BASED DOSAGE SCHEDULING

CROSS REFERENCE

The present patent application filed on Dec. 6, 2011 claims the benefit of provisional patent application 61/420,151 filed on Dec. 6, 2010, and this patent application claims the benefit of provisional patent application 61/420,140 filed on Dec. 6, 2010, and this patent application claims the benefit of provisional patent applications 61/486,427 and 61/486,436 both filed on May 16, 2011, and this patent application claims the benefit of provisional patent application 61/498,489 filed on Jun. 17, 2011, and is a continuation-in-part of patent application Ser. No. 12/945,709 filed on Nov. 12, 2010 entitled SYSTEM AND METHOD FOR ONLINE INTEGRATED MULTIPLE TABLET ORDERING, and is a continuation-in-part of patent application Ser. No. 12/896,284 filed on Oct. 1, 2010 entitled SYSTEM AND METHOD FOR GENERATING AN INTEGRATED LABEL FOR CONTAINER HOUSING MULTI-SCRIPT POUCHES that claims the benefit of provisional patent application 61/248,471 filed on Oct. 4, 2009, and is a continuation-in-part of patent application Ser. No. 12/896,275 filed on Oct. 1, 2010 entitled SYSTEM AND METHOD FOR INTEGRATED VERIFICATION AND ASSEMBLY OF MULTI-SCRIPT POUCHES INTO A HOUSING CONTAINER that claims the benefit of provisional patent application 61/248,471 filed on Oct. 4, 2009, and is a continuation-in-part of patent application Ser. No. 12/896,134 filed on Oct. 1, 2010 entitled SYSTEM AND METHOD FOR COMBING DIFFERENT TABLETS INTO A POUCH that claims the benefit of provisional patent application 61/248,471 filed on Oct. 4, 2009, and is a continuation-in-part of patent application Ser. No. 12/891,042 filed on Sep. 27, 2010 entitled LOW VISION PATIENT COMPLIANT MEDICATION MANAGEMENT SYSTEM AND METHOD that claims the benefit of provisional patent application 61/245,912 filed on Sep. 25, 2009, and is a continuation-in-part of patent application Ser. No. 12/891,029 filed on Sep. 27, 2010 entitled DUAL DISPENSING TABLET CONTAINER that claims the benefit of provisional patent application 61/245,899 filed on Sep. 25, 2009, and is a continuation-in-part of patent application Ser. No. 12/696,884 filed on Jan. 29, 2010 entitled SYSTEM AND METHOD FOR VERIFYING ANS ASSEMBLING A MULTIPLE PRESCRIPTION PACKAGE that claims the benefit of provisional patent application 60/854,341 filed on Oct. 24, 2006, and is a continuation-in-part of patent application Ser. No. 12/684,640 filed on Jan. 8, 2010 entitled USER SELECTABLE MULTIPLE TABLET PACKAGE, and is a continuation-in-part of patent application Ser. No. 12/684,664 filed on Jan. 8, 2010 entitled SYSTEM AND METHOD FOR PLACING A MULTIPLE TABLET ORDER, and is a continuation-in-part of patent application Ser. No. 12/684,060 filed on Jan. 7, 2010 entitled SYSTEM AND METHOD FOR AUTOMATICALLY MANAGING INVENTORY IN A MULTIPLE TABLE PACKAGE which is a continuation-in-part of patent application Ser. No. 11/796,123 now U.S. Pat. No. 7,690,173, filed on Apr. 25, 2007 entitled MULTIPLE PRESCRIPTION PRODUCTION FACILITY, and is a continuation-in-part of patent application Ser. No. 12/631,586 filed on Dec. 4, 2009 entitled MULTIPLE PRESCRIPTION PRODUCTION FACILITY, and is a continuation-in-part of patent application Ser. No. 12/424,483 filed on Apr. 15, 2009 entitled MANUFACTURING SEPARABLE POUCHES WITH A CENTER CUT BLADE, and is a continuation-in-part of patent application Ser. No. 12/424,475 filed on Apr. 15, 2009 entitled TABLET DISPENSING CONTAINER that claims the benefit of provisional patent applications 61/045,160 filed Apr. 15, 2008, provisional patent application 61/045,166 filed Apr. 15, 2008, provisional patent application 61/045,171 filed Apr. 15, 2008, and is a continuation-in-part of patent application Ser. No. 12/418,436 filed on Apr. 3, 2009 entitled CHILD PROOF MEDICATION PACKAGING SYSTEM AND METHOD, and is a continuation-in-part of patent application Ser. No. 12/418,418 filed on Apr. 3, 2009 entitled SPIRAL MEDICATION PACKAGING SYSTEM AND METHOD, and is a continuation-in-part of patent application Ser. No. 11/796,125 filed on Apr. 25, 2007 entitled SYSTEM AND METHOD FOR PROCESSING A MULTIPLE PRESCRIPTION ORDER, and is a continuation-in-part of patent application Ser. No. 12/418,422 filed on Apr. 3, 2009 entitled PATIENT COMPLIANT MEDICATION MANAGEMENT SYSTEM AND METHOD that claims the benefit of provisional patent application 61/042,262 filed Apr. 3, 2008 and provisional patent application 61/042,263 filed on Apr. 3, 2008, and is a continuation-in-part of patent application Ser. No. 11/923,321 filed on Oct. 24, 2007 entitled METHOD FOR VERIFYING AND ASSEMBLING A MULTIPLE PRESCRIPTION PACKAGE that claims the benefit of provisional patent application 60/854,341 having a filing date of Oct. 24, 2006, and is a continuation-in-part of patent application Ser. No. 11/796,124 entitled MULTIPLE PRESCRIPTION PACKAGE AND METHOD FOR FILING THE PACKAGE that claims the benefit of provisional patent application 60/795,370 filed on Apr. 26, 2006, provisional patent application 60/795,446 having a filing date of Apr. 26, 2006, provisional patent application 60/795,413 having a filing date of Apr. 26, 2006, and is a continuation-in-part of patent application Ser. No. 11/241,783 entitled PILL ASSEMBLY FOR PILL PACKAGING AND DELIVERY SYSTEMS that claims the benefit of provisional patent application 60/615,267 having a filing date of Oct. 1, 2004, and all applications listed are hereby incorporated by reference.

FIELD

This description relates to a system and method for scheduling tablet dosages using a matrix input. More particularly, the description relates to an application that displays a matrix to allow designation of a quantity of tablets to be consumed during each period represented as an element of the matrix.

BACKGROUND

Compliance with a regimen of medication or supplements is challenging for patients having difficulty remembering when a dose has been consumed. The problem may be intensified when the quantity of tablets to be consumed varies over time.

One solution to the problem of compliance with a regimen involving consumption of varying amounts of tablets is to package the tablets with labeling indicating when the package contents are to be consumed. Thus, there is a need for a system having a scheduling input that allows a user to indicate different quantities of tablets to be consumed at different times.

Although systems exist for allowing a user to indicate varying tablet quantities to be consumed at different times, such systems lack a user-friendly matrix interface allowing the user to enter, view and verify the tablet quantities in a single window.

There is also a need for a system to generate a dosing schedule for labeling and packaging based on a matrix scheduling input. Although multiple prescription filling systems are available, e.g. the McKesson PACMED system, these systems have limited labeling capabilities. Additionally, these filling systems lack procedures to verify an order prior to packaging. Furthermore, these filling systems fail to provide a scheduling input allowing a user to indicate different tablet quantities to be consumed at different times.

It would thus be desirable to have a system to generate instructions for compliance packaging and labeling according to a scheduling input that allows a user to indicate different quantities of tablets to be consumed at different times.

SUMMARY

A system and method for scheduling tablet dosage is described. The system includes a computing device, a filling system, and a plurality of containers. The computing device hosts an application that includes a user interface receiving a prescription order including a designation for each tablet to be ordered. The user interface displays a scheduling matrix that includes cells, in which each cell receives a tablet quantity designation. The application generates a dosing schedule based on the tablet quantities entered into the scheduling matrix. The filling system receives an order from the application and the order includes the dosing schedule. The filling system controls one or more filling cells for automatically dispensing tablets in accordance with the dosing schedule. The containers are controlled by the filling system and receive the tablets dispensed by the filling system. At least one container includes a first tablet and a second tablet, wherein the first tablet has a first shape and a first color that is different from the second tablet.

In one embodiment, the system and method also includes an automated inspection module that performs an inspection of each container to identify the first tablet and the second tablet within each container. The automated inspection includes an inspection module that operates at visual wavelengths and analyzes each tablet color and each tablet shape.

In another illustrative embodiment, each container includes a pouch with a plurality of different tablets. Additionally, the plurality of pouches are received by a box that includes, a top wall having one end fixedly coupled to the box and an opposite end that provides a foldable lid, a front-side wall, a right-side wall that abuts the front-side wall and the to wall, a back-side wall that abuts the right-side wall and the top wall, a left-side wall that is between the back-side wall and the front-side wall, the left-side wall configured to abut the to wall, a bottom wall that abuts the front-side wall, the right-side wall, the back-side wall, and the left-side wall, and a cavity defined by the front-side wall, the right-side wall, the back-side wall, the left-side wall and the bottom wall. A code is then associated with one of the pouches and the code is also associated with the prescription. A label is affixed to the box, wherein the label includes a description of the medications and the code associated with the prescription. The cavity receives the plurality of filled pouches that are associated with the code. One of the walls receives the label associated with the code.

DRAWINGS

The present invention will be more fully understood by reference to the following drawings which are for illustrative, not limiting, purposes.

FIGS. 2 and 3A-3B show an illustrative scheduling matrix populated by automatic means.

FIG. 4 shows an illustrative verification interface of the application.

FIG. 5 shows an illustrative interface for changing tablet quantities in an existing schedule matrix.

DESCRIPTION

Figure 1:
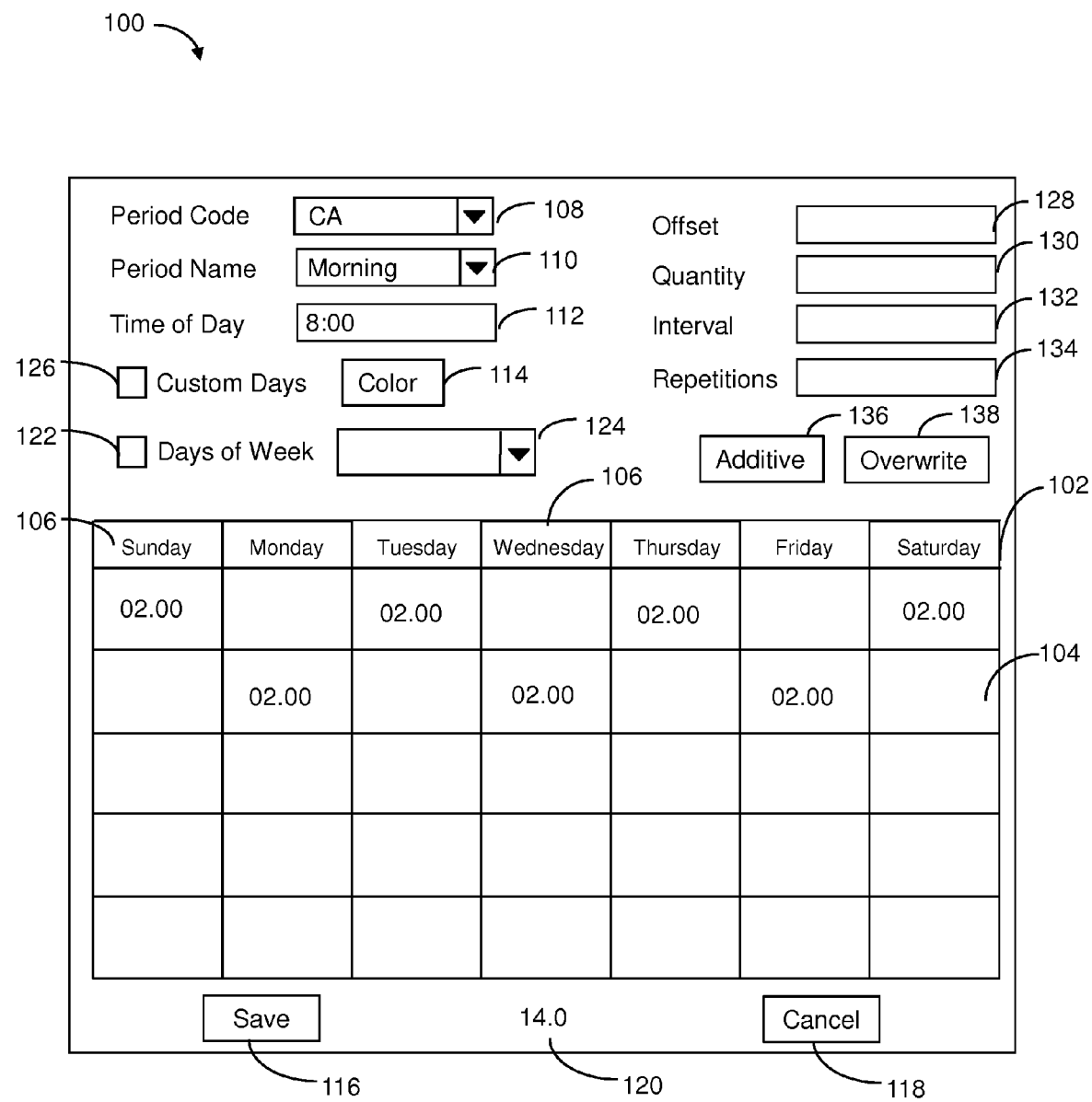
FIG. 1 is an illustrative scheduling matrix user interface.

Persons of ordinary skill in the art will realize that the following description is illustrative and not in any way limiting. Other embodiments of the claimed subject matter will readily suggest themselves to such skilled persons having the benefit of this disclosure. It shall be appreciated by those of ordinary skill in the art that the systems and apparatus described hereinafter may vary as to configuration and as to details. Additionally, the methods may vary as to details, order of the actions, or other variations without departing from the illustrative methods disclosed herein.

An application that allows a user to indicate dosage scheduling for the tablets is described. The application presents a user interface that allows the user to enter quantities of a particular tablet type to be consumed. The scheduling interface comprises a matrix. Each cell in the matrix represents a period of time, such as a day. The user may enter numbers into one or more of the cells, each number indicating a quantity of tablets to be consumed in the period of time represented by the cell.

For example, a prescription may indicate that a patient is to receive one tablet every day at bedtime for one week and two tablets every day at bedtime for the following three weeks. In an illustrative embodiment of the scheduling matrix, each cell of the matrix represents a day of the week. The scheduling matrix may comprise, for example, 35 cells. To produce a schedule for the illustrative prescribed tablet described above, the user of the application would enter the number one in the first seven cells of the matrix and would enter the number two in the next twenty-one cells of the matrix. Various automated means may be provided to allow rapid entry of the numbers in the scheduling matrix. The scheduling matrix interface may allow the user to indicate that the tablets indicated in the matrix are to be consumed at a particular dosing time, such as bedtime.

In some embodiments, the application is an online application hosted on a server and accessible via a network by a client. The user may select a particular tablet type from a database. In some embodiments, the database is stored on the same server on which the application is hosted. Alternatively, the database may be stored on a separate server. In addition to storing identification information for various tablet types, the database may store a plurality of information about the tablets, such as an image of the tablet, potential side effects, manufacturer, generic/brand name status, and whether a prescription is required for dispensing the tablet.

When the schedule has been completed, the application may generate an output comprising directions for filling packaging in accordance with the schedule. The application may be an ordering application that receives transactional information from the user and generates an order for tablets. A filling device may fill packages according to the schedule. In some embodiments, labels are printed and affixed to the package. The labels may indicate information comprising, for example, the contents of the package, dosing time for the package contents, and information pertaining to the patient to receive the package contents.

In this manner, compliance with a regimen of tablets, including a regimen in which different quantities of tablets are to be consumed at different times, is aided through the production of packaging containing the proper number of tablets for each dosing time.

The scheduling system described herein may operate with any front-end pharmacy solution. Additionally, the scheduling system may operate with any back-end automated filling robot.

The terms "tablet" and "tablets" as used herein may refer to any form of prescription medication, non-prescription medication, or supplement intended to be ingested by or administered to a patient to improve the patient's health or well being. The medication or supplement may be in the form of caplets, pills, capsules, powders, liquids, gels, or suppositories, including vitamins, supplements, herbal formulations, or combinations thereof.

The term "matrix" as used herein refers to an array of numbers. The matrix interface comprises a series of cells arranged in parallel columns. The cells in the interface are configured to receive a numerical input representing a quantity of tablets. The terms "schedule," "matrix," "dosing matrix" and "scheduling matrix" are used interchangeably herein.

Dosing may be indicated for a particular dosing time (e.g., 8:00 AM) or a particular period of time (e.g., morning, 8:00-10:00 AM). The terms "dosing time" and "dosing period" are used interchangeably herein.

Referring to FIG. 1, there is shown an illustrative scheduling matrix user interface 100. The scheduling matrix user interface is typically accessed through a tablet ordering application. Generally, a user would access the interface after having selected a tablet type and a dosing period. In such a case, the scheduling matrix allows the user to designate a dosing schedule for the selected tablet type and dosing period.

Scheduling matrix 102 is comprised of a series of cells 104 arranged in parallel columns. In the illustrative matrix, each cell represents a day. In other embodiments, cells may represent other periods of time, such as hours or dosing periods. Matrix 102 is shown with column headers 106, each column header indicating a day of the week.

In some embodiments, the user may fill in the scheduling matrix manually by selecting a cell and typing a number in the cell, the number corresponding to the quantity of tablets to be consumed on the day associated with the cell. In the example shown, the user has selected the first cell of the matrix and entered the number two, as indicated by the number two displayed under the column header labeled "Sunday." The user then selected the third cell of the matrix, under the header "Tuesday," and entered the number two. The user continued to select cells enter the number two every other day until two pills were indicated every other day for two weeks. As the user enters numbers in the matrix, a total tablet quantity 120 is updated to reflect the sum of all tablet quantities entered in the matrix. Because the user has entered the quantity two in seven cells of the scheduling matrix, the total quantity of tablets shown is 14, as indicated at 120.

In other embodiments, the user may fill in the scheduling matrix by automated means, as described with reference to FIG. 2.

The dosing schedule shown in scheduling matrix 102 is associated with a dosing period. The user interface may comprise a period code input 108 with a drop down menu to indicate a period code associated with a dosing period. The period code may be a two-letter code representing a period of time during which the tablets are to be consumed. It will be recognized that alternative coding systems may be used. The user interface may comprise a period name input 110 to indicate a period name associated with a dosing period. In some embodiments, the user may use either of inputs 108 or 110 to indicate a dosing period to associate with the schedule shown in scheduling matrix 102. In the illustrative interface, the schedule shown in matrix 102 is associated with a morning dosing time having period code "CA." When the period code has been selected at box 108, the period name in box 110 and time of day in box 112 are automatically populated with the corresponding values. Conversely, if the user selects a period name from the drop down menu at 110, the period code box 108 and time of day box 112 are automatically populated.

Additionally, the user interface may comprise a color code box 114 indicating a color associated with the selected dosage period. The color shown in color code box 114 may be printed on a label affixed to tablet packaging to aid the consumer in identifying the dosing period during which the tablets contained in a package are to be consumed.

When the user has completed entering the input into user interface 100, the user may save the input by activating save button 116. In some embodiments, the user interface will close when the save button is activated. If the user wishes to exit the user interface 100 without saving input, the user may select cancel button 118 to close the user interface. It will be recognized that other means for saving input and canceling out of the interface without saving may be used.

Check box 122 labeled "Days of the Week" allows a user to designate a day of the week to begin a dosing cycle in drop down menu 124. For example, it may be necessary or desirable for a patient to begin consuming prescribed tablets on a Wednesday. Referring to FIG. 2, check box 122 is checked, indicating that the day indicated in drop down menu 124, Wednesday, will begin the dosing cycle. Because box 122 is checked, Wednesday appears in column header 106 for the first column.

When check box 126 labeled "Custom Days" is checked, scheduling matrix 102 is shown without column headers 106, as shown in FIGS. 3A-3B. In some cases, it is not necessary for tablet consumption to begin on a particular day. Checking box 126 allows the application to generate an output indicating that labels will not specify a day of the week on which tablets are to be consumed. For example, the order could indicate that the labels should be numbered consecutively such that the package labeled "#1" (or similarly) is to contain the quantity of tablets indicated in the first cell, a package labeled "#2" (or similarly) is to contain the quantity of tablets indicated in the second cell, and so on.

It will be realized that a variety of inputs may be used in lieu of the check box, drop down menu, function buttons and text input boxes to indicate how the matrix should be displayed.

Text input boxes 128, 130, 132 and 134 labeled "Offset," "Quantity," "Interval," and "Repetitions," respectively, are used in conjunction with Additive button 136 and Overwrite button 138 to automatically populate the cells of the scheduling matrix. When the user activates Additive button 136, the input entered in input boxes 128-134 is applied to automatically populate the scheduling matrix. Each time the Additive button is activated, tablet quantities are added to the existing tablet quantities shown in the scheduling matrix according to the entered input. Activating Overwrite button 138 removes all existing tablet quantities in the matrix prior to populating the scheduling matrix according to the input entered in input boxes 128 and 134.

Referring now to FIG. 2, an illustrative dosage schedule populated automatically using input boxes 128-134 is shown. The user has entered 2 in the Offset input box 128. The offset input indicates the number of days between the first day of the scheduling matrix and the first day on which a tablet quantity designation is to be placed. In FIG. 2, the first day of the scheduling matrix is a Wednesday. Thus, when the offset setting is applied, the first day on which a tablet quantity is entered will be Friday. The user has entered 4 in the Quantity input box 130. The quantity input indicates a tablet quantity to be entered in the matrix. Thus, on the first day on which a tablet quantity is entered, Friday, the tablet quantity is set to 04.00. The user has entered 3 in the Interval input box 132. The interval input indicates a number of days between successive days to receive a tablet quantity entry. Thus, the next tablet quantity entry after the entry on Friday occurs on the following Monday, which is three days after Friday. The user has entered 5 in the Repetition input box 134. The repetition input indicates a number of days to repeat the tablet quantity designation as defined by the offset input, the quantity input, and the interval input. Thus, the entry of tablet quantity 4 is repeated five times at an interval of 3 days with an initial offset of two days from the first day indicated in the scheduling matrix, as shown in FIG. 2.

Referring now to FIGS. 3A-3B, an illustrative dosage schedule populated automatically and additively is shown. As indicated above, because Custom Days check box 126 is checked, the schedule is shown without headers. Thus, consumption of tablets is not scheduled to begin on a specified day. The schedule shown in FIG. 3A has been populated according to the input entered into boxes 128-134. To achieve the schedule shown in FIG. 3A, the user entered input in boxes 128-134 and activated the additive button. When the additive button was activated, the numbers appeared in the scheduling matrix. In this manner, the user was able to rapidly indicate that one tablet is to be consumed every day for the first week. To add a different quantity for the following weeks, the user enters new input in boxes 128-134 as shown in FIG. 3B. When the Additive button is activated, the second set of quantities is automatically inserted into the schedule as shown in FIG. 3B.

Referring now to FIG. 4, a verification interface of the application is shown. The verification interface comprises a scanned prescription 402 shown adjacent to a verification pane 404. The user may verify that information entered into the application is accurate by comparing the information shown in the scanned prescription to the information shown in the verification pane. The verification interface may also comprise an image 406 of tablets to allow verification that the tablet entered into the application is correct based on the information shown in the prescription. If the information is correct, the user may activate Approve button 412 to indicate that verification has taken place. The verification window also comprises a Matrix button 408. The Matrix button may be inactive if the order shown does not have an associated scheduling matrix. If the Matrix button is active, the initial day of the week of the associated scheduling matrix may be shown in drop down menu 110. When an active Matrix button is activated, the interface shown in FIG. 5 appears. The scheduling matrix shown in FIG. 5 allows the user to change tablet quantities previously inserted into a scheduling matrix associated with a particular tablet type for a particular patient. In some cases, the user may wish to change the initial day shown in the matrix, for example, because the current dispensation of tablets will begin on a different day from the previous dispensation of tablets. To change the initial day, the user may select the desired initial day from drop down menu 412. The day selected from drop down menu 412 will be shown in the column header of the first column of the matrix in FIG. 5.

Figure 6:
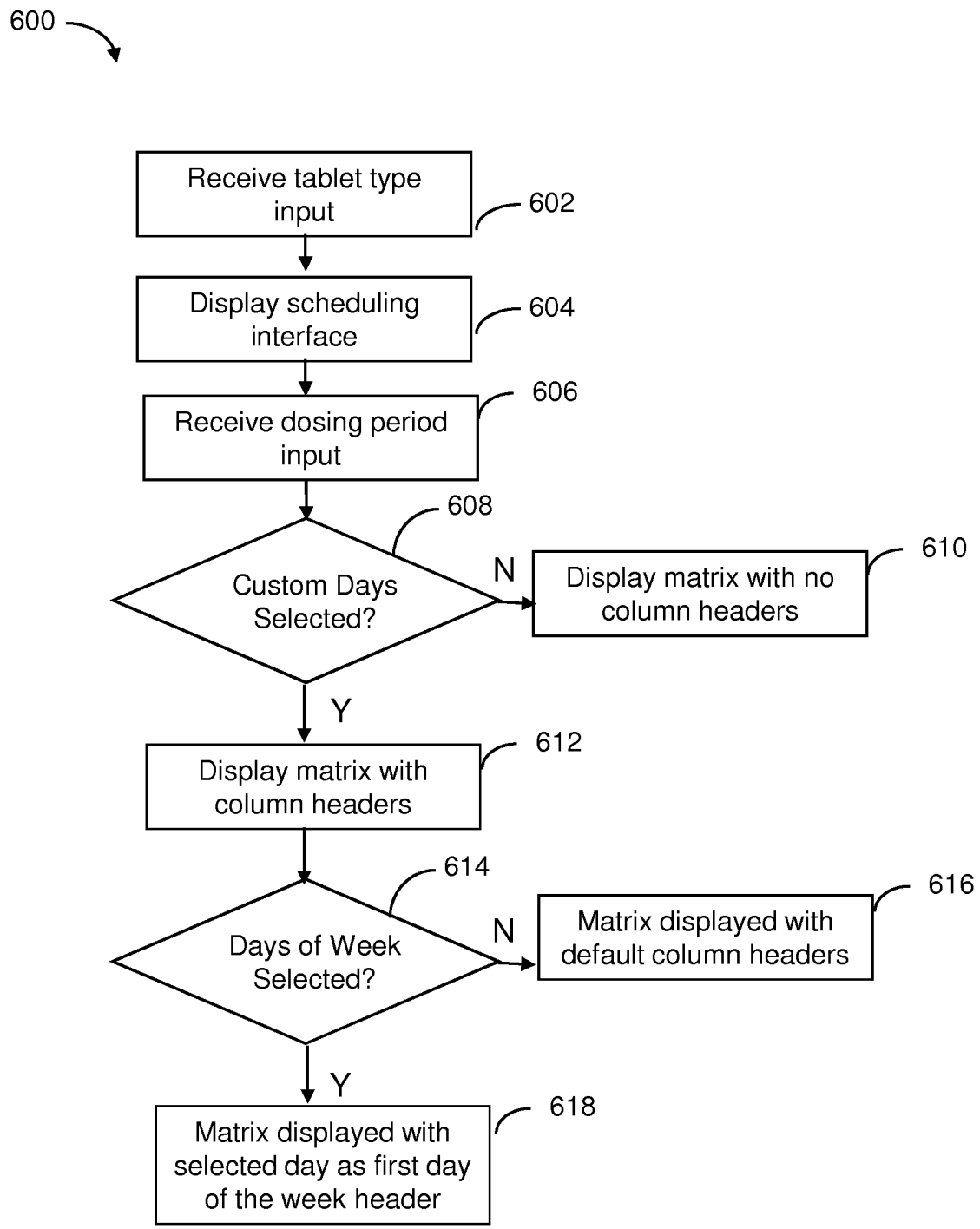
FIG. 6 shows an illustrative flowchart for displaying a matrix for dosage scheduling.

Referring now to FIG. 6, there is shown an illustrative flowchart of a method for displaying a matrix for dosage scheduling. The method begins at block 602, at which the application receives an input indicating a tablet type requiring matrix scheduling. The input may involve selecting a tablet type from a list of available tablet types. In some embodiments, the user will search a database to determine which tablet type to select. After a tablet type has been selected, the application may present a scheduling interface such as the interface shown in FIG. 1. In some embodiments, the user selects an option from an application menu to show the scheduling interface. In other embodiments, the scheduling interface may appear automatically when a tablet type has been selected. It will be recognized that a variety of methods may be used for displaying a scheduling interface with an application.

The method proceeds to block 606, at which the application receives a dosing period input. The dosing period input may be a period code or a period name. The dosing period indicates at which point during the time indicated in the cells of the matrix the tablet or tablets are to be consumed. For example, the dosing period may indicate at which point during the day the tablets indicated in the scheduling matrix are to be consumed. At decision diamond 608, it is determined whether the custom days box 126 has been marked with a check. If the custom days box has not been checked, the matrix is displayed with no column headers as indicated at block 610. If the custom days box has been checked, the matrix is displayed with column headers corresponding to the days of the week as indicated at block 612. The method then proceeds to decision diamond 614, at which it is determined whether the days of the week box 122 has been marked with a check. If the days of the week box has not been checked, the matrix is displayed with a default day of the week as the header of the first column of the matrix, as indicated at block 616. In an illustrative embodiment, the matrix is displayed with Sunday as the header for the first column of the matrix by default. If the days of the week box has been checked, the matrix is displayed with the day selected in drop down menu 124 as the header for the first column of the matrix, as indicated at block 618.

Figure 7:
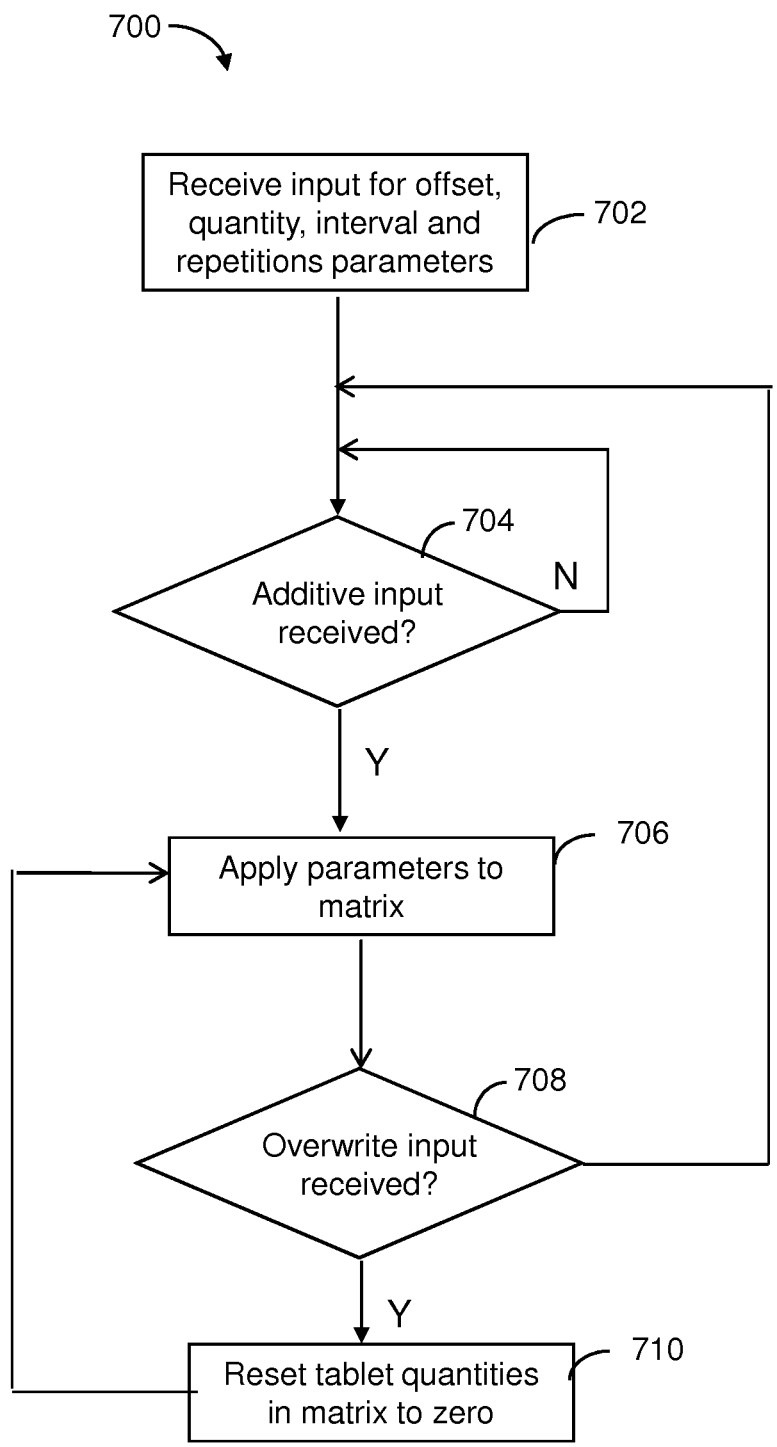
FIG. 7 shows an illustrative flowchart for automatically populating a scheduling matrix with tablet quantities.

Referring now FIG. 7, there is shown an illustrative flowchart for automatically populating a scheduling matrix with tablet quantities. The method begins at block 702, at which the application receives inputs for offset, quantity, interval and repetitions parameters in text input boxes 128-134. The method proceeds to decision diamond 704, at which the application determines whether an additive input has been received. If the additive button has been activated, the application inserts tablet quantities into the cells of the matrix according to the parameters indicated in text input boxes 128-134, as indicated at block 706. The application will add new tablet quantities to any existing tablet quantities in the same cell each time the additive button is activated. The method proceeds to decision diamond 708, at which the application determines whether an overwrite input has been received. If the overwrite button has been activated, the application sets the tablet quantity in each cell of the matrix to zero before inserting tablet quantities into the cells of the matrix, as indicated at block 710.

Figure 8:
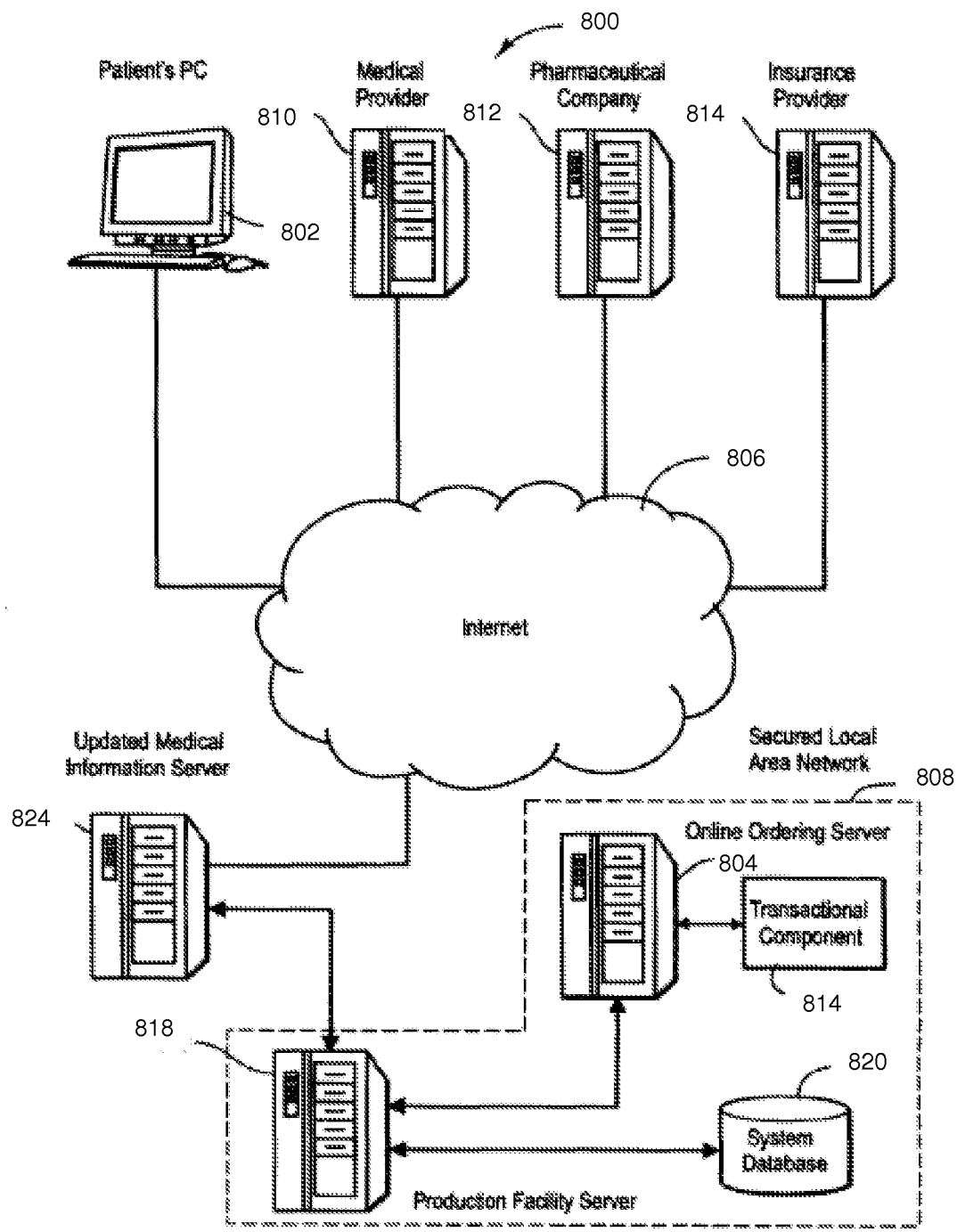
FIG. 8 shows an illustrative network architecture for an online dosage scheduling application.

Referring to FIG. 8, there is shown an illustrative block diagram system 800 for providing access to the application on a client via a server. The system comprises a client 802, a server 804, and a network 806. The network may be a wide area network (WAN) such as the Internet, or a local area network (LAN). In some embodiments, the online application may be viewed using a standard web browser.

Additional servers may be accessible to the application via the network, such as a medical provider server 810, a pharmaceutical company server 812 and an insurance provider server 814. The application may access information on these servers to determine, for example, billing information, patient coverage for pharmaceutical products, tablets to be made available through the application, and prescription information. In some embodiments, a transactional component 814 hosted on server 804 facilitates financial transactions for ordering tablets according to the schedule matrix.

The system may further comprise production facility server 818. The production server is associated with managing the inventory in the production facility. The production server may comprise an inventory database module 820 that determines if the production facility can satisfy the tablet order. Ordering server 804 may also comprise a database indicating tablet types available through the application, patient information, prescriber information, and so on. Alternatively, the application may obtain such information from one or more databases hosted on one or more separate servers, such as the servers indicated at 810-814. In some embodiments, production server 818 and online server 804 are part of secure LAN 208.

The client is able to place a scheduled tablet order using the application. In one illustrative example, a pharmacist's on-line server communicates with the production server 818 and the inventory database 820. The pharmacist's on-line server makes a request to determine whether the production facility can satisfy the pharmacist's order. The inventory database is accessed to determine if the tablet order may be filled. Once the pharmacist's online server has received confirmation that the prescription order can be filled, the online server relays this information back to the client's computer via the Internet.

The production server 818 also communicates the order to production facility computers which control the various systems and subsystems involved in producing the tablet assembly, including printers for labeling the lidstock on each individually sealed container with dosing instructions such as date and time to take the tablets in each individual container. The production server may also communicate to production facility computers which are connected to a printer for labeling an area of the sleeve portion of the tablet assembly, with end user information, drug information and expiration date(s) for the medication stored within the individual containers.

The online ordering server 804 and the production facility server 818 may also be communicatively connected to an updated medical information server 824 via a network such as the Internet or a secure wide area network connection. The updated medical information server 824 may be a private or government maintained server with compiled updated information on the various drugs stored in the production facility. The updated information may comprise new warnings on drug interactions, updated expiration dates, toxicity information and the like. The updated information is communicated to the second labeling component. This information is valuable in assuring the multi-drug prescriptions are effective and safe.

Figure 9A:
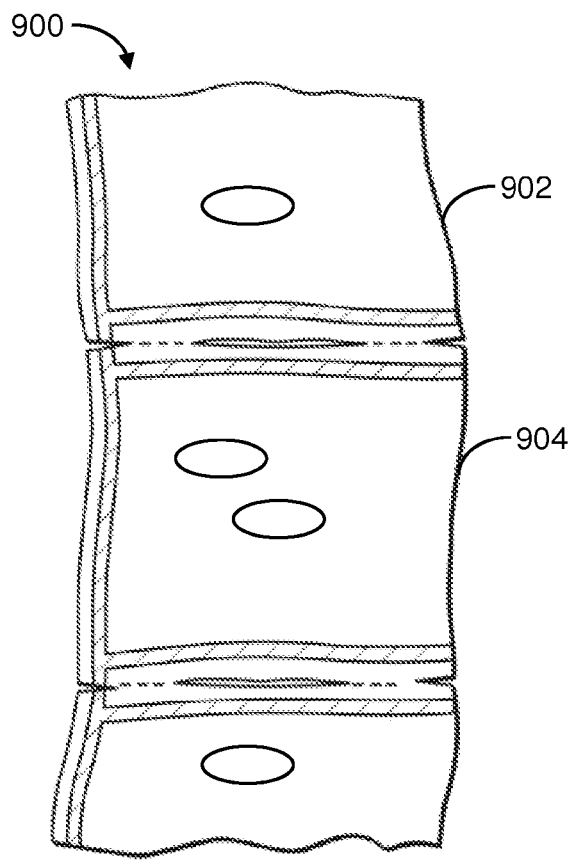
FIG. 9A shows illustrative packaging filled in accordance with a dosing schedule.
Figure 9B:
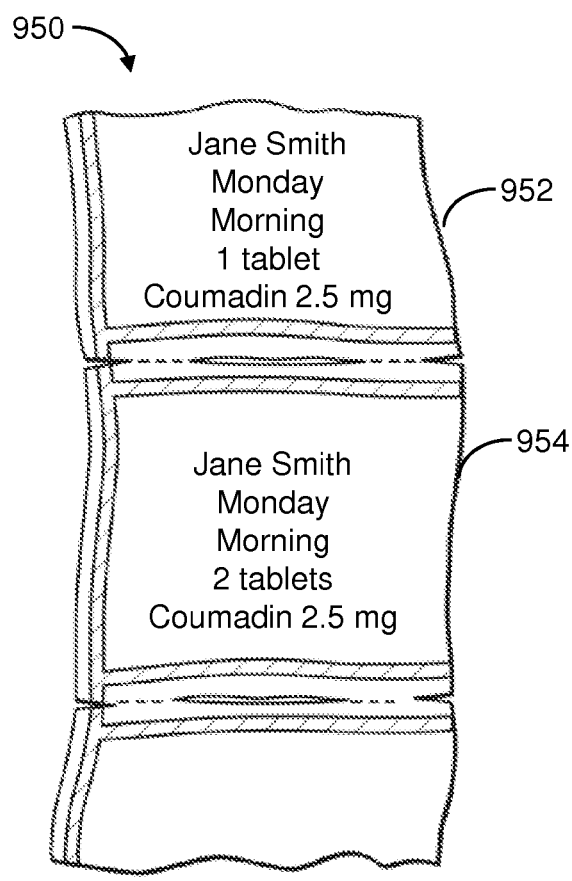
FIG. 9B shows illustrative labels for the packaging shown in FIG. 9A.

Referring now to FIG. 9A, an illustrative set of pouches 900 filled in accordance with a dosing schedule is shown. In some embodiments, the pouches comprise a transparent material that allows the contents of the pouch to be viewed for verification. The pouches shown in the illustrative embodiment have been filled in accordance with a dosing schedule that indicates one tablet to be taken on Monday during the Morning dosing period, two tablets to be taken on Tuesday during the Morning dosing period, and one tablet to be taken on Wednesday during the Morning dosing period. One tablet is visible within pouch 902, which corresponds to the Monday dose and two tablets are visible within pouch 904, which corresponds to the Tuesday dose. The pouches may be separably coupled to one another, for example, via a perforated material joining adjacent pouches. Labels with information regarding the contents of the pouches may be affixed to the pouches as shown in FIG. 9B. In this manner, the consumer or a caregiver may verify that the tablets have been consumed in conformance with the dosing schedule indicated in the application by checking the label of the pouch at the dosing time.

Referring to FIG. 9B there is shown illustrative labeling 954 for the pouches shown in FIG. 9A. By way of example and not of limitation, the illustrative label 952 may contain written information that is related to each tablet such as summary information about each tablet, day of the week on which the dose is to be consumed, dosing period during which the dose is to be consumed, summary information about the patient, the name of the patient, an image of the patient, images of the first tablet and the second tablet that may be to scale, a drug interaction description, or any combination thereof.

The illustrative label may include an image of the particular patient, and the name and address of the patient. Furthermore, there may be additional unique information about the patient printed on the label, such as the doctor's name and telephone number, and patient health insurance information. Additionally, there may be a particular description about each tablet that may include manufacturer's latest labeling information, a summary of expected side effects, and a short description of possible drug interactions. This information may be presented in a manner similar to the Physician's Desk Reference, which includes a color picture of each pill with summary information about the tablet. Additionally, information about how to administer products may be provided. This information may be used by a caregiver to help in dispensing the appropriate medications.

It is to be understood that the foregoing is a detailed description of illustrative embodiments. The scope of the claims is not limited to these specific embodiments. Various elements, details, execution of any methods, and uses can differ from those just described, or be expanded on or implemented using technologies not yet commercially viable, and yet still be within the inventive concepts of the present disclosure. The scope of the invention is determined by the following claims and their legal equivalents.

What is claimed is:

1. A system for scheduling tablet dosage with visual inspection, the system comprising:
   a computing device hosting an application comprising a user interface receiving a prescription order including a designation for each tablet to be ordered;
   the user interface configured to display a scheduling matrix, the scheduling matrix comprising a plurality of cells, each cell receiving a tablet quantity designation;
   the application generating a dosing schedule based on the tablet quantities entered into the scheduling matrix;
   a filling system receiving an order from the application, the order including the dosing schedule, the filling system controlling one or more filling cells for automatically dispensing tablets in accordance with the dosing schedule;
   a plurality of containers controlled by the filling system, the plurality of containers receiving the tablets dispensed by the filling system, wherein at least one container includes a first tablet and a second tablet, the first tablet having a first shape and a first color that is different from the second tablet; and
   an automated inspection module for performing an inspection of each container to identify the first tablet and the second tablet within each container, wherein the automated inspection includes an inspection module that operates at visual wavelengths and analyzes each tablet color and each tablet shape.

2. The system of claim 1, wherein the user interface receives parameters from a user, the user interface automatically populating the scheduling matrix according to the parameters.

3. The system of claim 2, wherein the parameters comprise an offset input indicating the number of days between the first day of the scheduling matrix and the first day on which a tablet quantity designation is to be placed.

4. The system of claim 3, wherein the parameters comprise a quantity input indicating a tablet quantity designation.

5. The system of claim 4, wherein the parameters comprise an interval input indicating a number of days between successive days to receive the tablet quantity designation.

6. The system of claim 5, wherein the parameters comprise a repetitions input indicating a number of days to repeat the tablet quantity designation as defined by the offset input, the quantity input, and the interval input.

7. The system of claim 1, wherein each container includes a pouch with a plurality of different tablets.

8. The system of claim 7, wherein the plurality of pouches are received by a box that includes,
   a top wall having one end fixedly coupled to the box and an opposite end that provides a foldable lid;
   a front side wall;
   a right-side wall that abuts the front side wall and the top wall;
   a back side wall that abuts the right-side wall and the top wall;
   a left-side wall that is between the back side wall and the front side wall, the left-side wall configured to abut the top wall;
   a bottom wall that abuts the front side wall, the right-side wall, the back side wall, and the left-side wall;
   a cavity defined by the front side wall, the right-side wall, the back side wall, the left-side wall and the bottom wall;
   a code associated with one of the pouches, wherein the code is associated with the prescription;
   a label affixed to the box, wherein the label includes a description of the medications and the code associated with the prescription;
   wherein the cavity is configured to receive the plurality of filled pouches that are associated with the code; and
   wherein one of the walls is configured to receive the label associated with the code.

9. The system of claim 3, wherein each container corresponds to a pouch that includes a plurality of different tablets, the plurality of pouches received by a box that includes,
   a top wall having one end fixedly coupled to the box and an opposite end that provides a foldable lid;
   a front side wall;
   a right-side wall that abuts the front side wall and the top wall;
   a back side wall that abuts the right-side wall and the top wall;
   a left-side wall that is between the back side wall and the front side wall, the left-side wall configured to abut the top wall;
   a bottom wall that abuts the front side wall, the right-side wall, the back side wall, and the left-side wall;
   a cavity defined by the front side wall, the right-side wall, the back side wall, the left-side wall and the bottom wall;
   a code associated with one of the pouches, wherein the code is associated with the prescription;
   a label affixed to the box, wherein the label includes a description of the medications and the code associated with the prescription;
   wherein the cavity is configured to receive the plurality of filled pouches that are associated with the code; and
   wherein one of the walls is configured to receive the label associated with the code.

10. A system for scheduling tablet dosage, the system comprising:
    a computing device hosting an application including a user interface, the user interface receiving a prescription order including a designation for each tablet to be ordered;
    the user interface displaying a scheduling matrix comprising a plurality of cells, each cell configured to receive a tablet quantity designation;
    generating a dosing schedule based on the tablet quantities entered into the scheduling matrix;
    a filling system receiving an order from the application, the order including the dosing schedule, the filling system controlling one or more filling cells for automatically dispensing tablets in accordance with the dosing schedule;
    a plurality of pouches receiving the tablets dispensed by the filling system, wherein each pouch includes a plurality of different tablets, in which a first plurality of tablets are different from a second plurality of tablets; and
    a box that receives the plurality of pouches, wherein the box includes,
    a top wall having one end fixedly coupled to the box and an opposite end that provides a foldable lid;
    a front side wall;
    a right-side wall that abuts the front side wall and the top wall;
    a back side wall that abuts the right-side wall and the top wall;
    a left-side wall that is between the back side wall and the front side wall, the left-side wall configured to abut the top wall;
    a bottom wall that abuts the front side wall, the right-side wall, the back side wall, and the left-side wall;

a cavity defined by the front side wall, the right-side wall, the back side wall, the left-side wall and the bottom wall;

a code associated with one of the pouches, wherein the code is associated with the prescription order;

a label affixed to the box, wherein the label includes a description of the medications and the code associated with the prescription;

wherein the cavity is configured to receive the plurality of filled pouches that are associated with the code; and wherein one of the walls is configured to receive the label associated with the code.

11. The system of claim 10, wherein the user interface receives parameters from a user, the user interface automatically populating the scheduling matrix according to the parameters.

12. The system of claim 11, wherein the parameters comprise an offset input indicating the number of days between the first day of the scheduling matrix and the first day on which a tablet quantity designation is to be placed.

13. The system of claim 12, wherein the parameters comprise a quantity input indicating a tablet quantity designation.

14. The system of claim 13, wherein the parameters comprise an interval input indicating a number of days between successive days to receive the tablet quantity designation.

15. The system of claim 14, wherein the parameters comprise a repetitions input indicating a number of days to repeat the tablet quantity designation as defined by the offset input, the quantity input, and the interval input.

16. The system of claim 10, further comprising an automated inspection module for performing an inspection of each pouch to identify the first tablet and the second tablet within each container, wherein the automated inspection includes an inspection module that operates at visual wavelengths and analyzes each tablet shape.

17. The system of claim 11, wherein the inspection module analyzes each tablet color.

18. A method for scheduling tablet dosage with visual inspection, the method comprising:
receiving a multiple prescription order with a user interface of an application, the multiple prescription order including a designation of a tablet to be ordered, the application hosted on a computing device;
displaying a scheduling matrix in the user interface, the scheduling matrix comprising a plurality of cells, each cell configured to receive a tablet quantity designation;
generating a dosing schedule with the application based on the tablet quantities entered into the scheduling matrix;
receiving an order including the dosing schedule with a filling system;
dispensing tablets with the filling system in accordance with the dosing schedule, the filling system automatically controlling one or more filling cells for automatically dispensing tablets to containers;
receiving automatically the tablets dispensed by the filling system in a plurality of containers, wherein at least one container includes a first tablet and a second tablet, the first tablet having a first shape and a first color that is different from the second tablet; and
performing an automated inspection of each container to identify the first tablet and the second tablet within each container with an automated inspection module, wherein the automated inspection includes an inspection module that operates at visual wavelengths and analyzes each tablet color and each tablet shape.

19. The method of claim 18, further comprising receiving parameters from a user for populating the scheduling matrix, and automatically populating the scheduling matrix according to the parameters.

20. The method of claim 19, wherein the parameters comprise an offset input indicating the number of days between the first day of the scheduling matrix and the first day on which a tablet quantity designation is to be placed.

21. The method of claim 20, wherein the parameters comprise a quantity input indicating a tablet quantity designation.

22. The method of claim 21, wherein the parameters comprise an interval input indicating a number of days between successive days to receive a tablet quantity designation.

23. The method of claim 22, wherein the parameters comprise a repetitions input indicating a number of days to repeat the tablet quantity designation as defined by the offset input, the quantity input, and the interval input.

24. The method of claim 18, wherein each container is a pouch.

25. The method of claim 24 further comprising,
receiving the plurality of pouches in a box that includes,
a top wall having one end fixedly coupled to the box and an opposite end that provides a foldable lid;
a front side wall;
a right-side wall that abuts the front side wall and the top wall;
a back side wall that abuts the right-side wall and the top wall;
a left-side wall that is between the back side wall and the front side wall, the left-side wall configured to abut the top wall;
a bottom wall that abuts the front side wall, the right-side wall, the back side wall, and the left-side wall;
a cavity defined by the front side wall, the right-side wall, the back side wall, the left-side wall and the bottom wall;
associating a code with one of the pouches, wherein the code is associated with the multiple prescription order;
affixing a label to the box, wherein the label includes a description of the medications and the code associated with the prescription;
receiving the plurality of filled pouches that are associated with the code in the box; and
receiving the label associated with the code in one of the walls.

* * * * *